(12) United States Patent
Tomita et al.

(10) Patent No.: US 10,105,307 B2
(45) Date of Patent: Oct. 23, 2018

(54) MAKEUP COSMETIC AND MAKEUP KIT COMPRISING THE MAKEUP COSMETIC AND A TOP COATING AGENT

(75) Inventors: Noriko Tomita, Kanagawa (JP);
Hirotaka Takada, Kanagawa (JP);
Hiroyuki Kakoki, Kanagawa (JP);
Takashi Minami, Kanagawa (JP);
Yoriko Mune, Kanagawa (JP);
Takayuki Miyazaki, Kanagawa (JP);
Yuko Suzuki, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 292 days.

(21) Appl. No.: 13/577,032

(22) PCT Filed: Jan. 28, 2011

(86) PCT No.: PCT/JP2011/051783
§ 371 (c)(1),
(2), (4) Date: Aug. 24, 2012

(87) PCT Pub. No.: WO2011/096337
PCT Pub. Date: Aug. 11, 2011

(65) Prior Publication Data
US 2012/0312316 A1    Dec. 13, 2012

(30) Foreign Application Priority Data

Feb. 5, 2010   (JP) ................................. 2010-023699
Mar. 11, 2010  (JP) ................................. 2010-053922

(51) Int. Cl.
| | |
|---|---|
| *A61K 8/81* | (2006.01) |
| *A61Q 1/02* | (2006.01) |
| *A61Q 1/06* | (2006.01) |
| *A61Q 1/10* | (2006.01) |
| *A61K 8/31* | (2006.01) |
| *A61K 8/891* | (2006.01) |

(52) U.S. Cl.
CPC .............. *A61K 8/8111* (2013.01); *A61K 8/31* (2013.01); *A61K 8/891* (2013.01); *A61Q 1/02* (2013.01); *A61Q 1/06* (2013.01); *A61Q 1/10* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,961,998 | A | * | 10/1999 | Arnaud et al. ................. 424/401 |
| 2001/0031269 | A1 | | 10/2001 | Arnaud |
| 2004/0009198 | A1 | * | 1/2004 | Bernard et al. ................. 424/401 |
| 2004/0052745 | A1 | * | 3/2004 | Bernard et al. ............. 424/70.11 |
| 2006/0127339 | A1 | * | 6/2006 | Bavouzet et al. ......... 424/70.12 |
| 2008/0194715 | A1 | | 8/2008 | Wendel et al. |
| 2008/0305068 | A1 | * | 12/2008 | Zheng et al. ............... 424/78.03 |
| 2011/0142774 | A1 | * | 6/2011 | Tomita et al. .................. 424/64 |

FOREIGN PATENT DOCUMENTS

| | | |
|---|---|---|
| DE | 10 2004 027 837 | 3/2005 |
| EP | 0 498 119 | 12/1991 |
| EP | 1 303 246 | 4/2003 |
| EP | A 1454621 | 9/2004 |
| FR | 2 801 785 | 6/2001 |
| JP | A 61-65809 | 4/1986 |
| JP | 63139107 | 6/1988 |
| JP | A 7-316016 | 12/1995 |
| JP | A 8-26936 | 1/1996 |
| JP | A 10-508867 | 6/1996 |
| JP | A 8-295614 | 11/1996 |
| JP | 11071237 | 3/1999 |
| JP | 2001199846 | 7/2001 |
| JP | 2002154916 | 5/2002 |
| JP | A 2002-154916 | 5/2002 |
| JP | 2002275018 | 9/2002 |
| JP | 2004503574 | 2/2004 |
| JP | 2007-238578 | * 9/2007 |
| JP | 2010-24163 | 2/2010 |
| JP | A 2010-24163 | 2/2010 |
| WO | WO 2005/097046 | 10/2005 |

(Continued)

OTHER PUBLICATIONS

JPO English language machine translation of JP-2007-238578, 2013.*
Wacker Silicones product information sheet for Belsil® PDM 1000 dated Oct. 30, 2011; http://www.brenntagspecialties.com/en/downloads/Products/Personal_care/WackerSilicones/Belsil_PDM_1000_TDS.pdf.*

(Continued)

*Primary Examiner* — David J Blanchard
*Assistant Examiner* — Alissa Prosser
(74) *Attorney, Agent, or Firm* — Andrew F. Young, Esq.; Lackenbach Siegel, LLP

(57) ABSTRACT

Provided is a makeup cosmetic which has a good feeling of use, without showing tautness or stiffness as in the case of using a silicone-based resin film or an offensive odor as in the case of using polyisoprene, and exhibits a good effect of preventing color migration. This makeup cosmetic is characterized by comprising polyisobutylene having a relative mass of 30,000-100,000 and a volatile hydrocarbon oil. Also provided are a top coating agent, which can be appropriately applied on the aforesaid makeup cosmetic, imparts glossiness and shows little color migration or blurring, a makeup kit comprising the aforesaid makeup cosmetic and the top coating agent, and a makeup method using the makeup kit.

6 Claims, No Drawings

(56) References Cited

FOREIGN PATENT DOCUMENTS

WO    WO 2007/008575     1/2007
WO    WO 2009/150852   * 12/2009

OTHER PUBLICATIONS

PCT/JP2011/051783 International Search Report dated Jan. 18, 2011, 2 pages—Japanese, 2 pages—English.
EP 11739686.1, European International Search Report from the European Patent Office, dated Feb. 4, 2016, 11 pages—English.

* cited by examiner

MAKEUP COSMETIC AND MAKEUP KIT COMPRISING THE MAKEUP COSMETIC AND A TOP COATING AGENT

CROSS REFERENCE TO RELATED APPLICATIONS

This application claims priority to International Ser. No. PCT/JP2011/051783 filed Jan. 28, 2011, the entire contents of which are incorporated herein fully by reference, which in turn claims priority to JP Ser. No. JP 2010-023699, filed on Feb. 5, 2010, and JP 2010-053922, filed on Mar. 11, 2010

TECHNICAL FIELD

The present invention relates to a makeup cosmetic and a makeup kit including the makeup cosmetic and a top coating agent. More specifically, the invention relates to a makeup cosmetic which is excellent in transfer resistance and less subject to makeup deterioration as well as attains good feeling of use, a top coating agent which is particularly suitably applied over the makeup cosmetic, imparts transparent glossiness, effectively prevents color transfer to a cup or the like, is excellent in use feeling and stability, and is free from smudge, as well as a makeup kit including the makeup cosmetic and the top coating agent, and a makeup method using the makeup kit.

BACKGROUND ART

In conventional makeup cosmetics, secondary adhesion, i.e. transfer of a lipstick, for example, from the lips to a cup or the like after applying the lipstick, has become a problem. The problem of the secondary adhesion has also been observed with a foundation wherein an applied cosmetic is adhered to clothes or the like, and the secondary adhesion is called as "makeup deterioration", which also includes a phenomenon that the cosmetic is clumped by perspiration and sebum.

Accordingly, a product which is obtainable by incorporating volatile and/or nonvolatile silicone oil and a hydrocarbon oil in various combinations has been proposed as a makeup cosmetic which hardly causes the secondary adhesion, i.e., is excellent in transfer resistance and less subject to makeup deterioration.

For example, Patent Document 1 discloses a makeup cosmetic containing an organic silicone resin having a specific structure, a volatile silicone oil, and a powder and describes that the makeup cosmetic is excellent in makeup deterioration prevention effect, is favorably spread, and attains refreshing use feeling. However, a coating formed by the silicone-based resin is hard to impart tautness and stiffness and to entail dryness.

Further, Patent Document 2 discloses a soft type oil-based makeup cosmetic which contains a hydrocarbon-based resin and a liquid oil component at least containing a volatile liquid hydrocarbon oil and a liquid silicone oil, and an oil gelling agent and/or a solid oil component and describes that the cosmetic is excellent in use feeling, hardly causes skin trouble, and is excellent in makeup lasting quality. However, since the liquid silicone oil which is contained as the essential component sometimes prevents formation of a coating of the hydrocarbon-based resin, it is difficult to attain satisfactory color transfer prevention effect.

Meanwhile, in Patent Document 3, a combinable composition containing a proadhesive substance (pressure sensitive adhesive) selected from polyisobutylenes having a relative molar mass of 150,000 to 2,200,000 and a makeup or care kit including a diffusible compound selected from polyisobutylenes having a relative molar mass of 445 to 10,000 are described, and it is described that they have good long-lasting property and excellent transfer resistance. However, the cosmetic containing polyisobutylene having molecular weight of 100,000 or more causes stringing after formation of a coating, and the phenomenon is not improved by the combination with polyisobutylene having a molecular weight of 100,000 or less, resulting in problems of degraded finish glossiness and, further, unpleasantness.

Further, in Patent Document 4, a cosmetic containing polyisoprene having a molar mass of 100,000 to 4,000,000, organic modified smectite, and a hydrocarbon-based oil component is described, and the cosmetic is described to be excellent in transfer resistance due to a coating formation property of polyisoprene. However, polyisoprene have a strong material odor and causes unpleasantness in use to entail a problem of necessitating strong perfuming for commercialization.

Under the circumstances, there still is a demand for a makeup cosmetic which hardly or never causes the secondary adhesion and is excellent in use feeling.

Meanwhile, as a means for suppressing the secondary adhesion of a makeup cosmetic, improving long-lasting property of the makeup cosmetic, and enhancing a makeup effect by adding glossiness to the lips, a method of applying a top coating agent (also called a lip coat, a lipstick overcoat, or the like) over the makeup cosmetic has been known.

Cosmetics commercialized as top coating agents can be classified into "emulsion type" and "oily type" depending on the form. The emulsion type is, as described in Patent Document 5, for example, an oil-in-water type emulsion cosmetic containing a water-repellant and oil-repellant oil component such as perfluoropolyether and dimethylpolysiloxane and a specific powder, and the oily type is a makeup cosmetic containing as a main component the water-repellant and oil-repellant oil component, various powders, and the like (Patent Documents 6 and 7).

However, though the emulsion type top coating agent is satisfactory in terms of a property of maintaining cosmetic effect of a lipstick or the like, suppression of color transfer, and improvement in usability, it has problems of insufficient glossiness-imparting effect and inferior transparency.

In turn, as the oily type top coating agent, for example, Patent Document 6 discloses an oily lip coat containing dimethylpolysiloxane having a low viscosity (10 to 300 cs at 25° C.) and anhydrous silicate, and optionally volatile silicone, while Patent Document 7 discloses a lipstick overcoat containing fluorine-modified silicone and a specific powder. It is described that each of them solves the problems detected with the conventional cases of using perfluoropolyether, and that a lipstick overcoat which is excellent in color transfer prevention effect is obtained. Further, Patent Document 8 and Patent Document 9 describe an oily lip coat containing a low viscosity (1,000 cs or less) silicone oil and fumed silica or anhydrous silicate and polymethylsilsesquioxane particles, which is described to be excellent in color transfer prevention effect.

However, the top coating agent containing as main component dimethylpolysiloxane as described in Patent Documents 5, 6, and 8 has problems that it tends to spread on the lip to smudge and is solubilized with the oil component which is generally used for lipsticks to cause smudge over time. Further, the fluorine-modified silicone described in Patent Documents 5 and 7 is inferior in glossiness and is not capable of attaining both of the effect of suppressing color transfer to a cup or the like and the glossiness. Further, the top coating agents described in Patent Documents 5 to 9 are intended to be applied over the lipstick or the like containing the conventional generally-used oil component and in some cases cause smudge depending on a composition of the lipstick or the like as a base.

PRIOR ART DOCUMENTS

Patent Document

Patent Document 1: JP-A Sho 61-65809
Patent Document 2: JP-A 2002-154916
Patent Document 3: JP-B 3947102
Patent Document 4: EP-A 1454621
Patent Document 5: JP-A Hei 7-316016
Patent Document 6: JP-A Hei 8-26936
Patent Document 7: JP-A Hei 8-295614
Patent Document 8: JP-A Hei 10-508867
Patent Document 9: JP-A 2010-24163

SUMMARY OF INVENTION

Problem to be Solved by the Invention

An object of the present invention is to provide a novel makeup cosmetic which is free from tautness and stiffness of conventional silicone-based resin coatings, free from odor problem of polyisoprene, has excellent use feeling, and has a good color transfer prevention effect.

At the same time, another object is to provide a top coating agent which is suitably used over the makeup cosmetic without being solubilized with an oil component used for the makeup cosmetic and, therefore, is suitably used as a makeup kit in combination with the makeup cosmetic, and, further, is capable of imparting satisfactory glossiness, suppressing color transfer, and suppressing smudge.

Means for Solving the Problem

In order to solve the above-described problems, the inventors have conducted extensive researches to find that it is possible to obtain a makeup cosmetic which is excellent in transfer resistance, is free from odor, and does not cause stringing by containing polyisobutylene which is a soft and adhesive hydrocarbon-based resin in combination with a volatile hydrocarbon oil and by using polyisobutylene having a molecular weight within a specific range as the polyisobutylene, thereby accomplishing the present invention.

Further, the inventors found that it is possible to prevent solubilization with an oil component used for the makeup cosmetic, to suppress color transfer and smudge, and to impart satisfactory glossiness by using methylphenylpolysiloxane having a viscosity higher than 1,000 as a top coating agent to be used in combination with the makeup cosmetic.

More specifically, the present invention encompasses:

(1) An oily makeup cosmetic containing polyisobutylene having a relative mass of 30,000 to 100,000 and a volatile hydrocarbon oil;

(2) The makeup cosmetic according to (1), which does not contain polyisobutylene of which a relative mass exceeds 100,000;

(3) The makeup cosmetic according to (1) or (2), further containing an organic modified clay mineral and/or a dextrin fatty acid ester;

(4) The makeup cosmetic according to any one of (1) to (3), further containing a solid oil component and/or a powder;

(5) The makeup cosmetic according to any one of (1) to (4), which is a lipstick, eye shadow, or a foundation;

(6) A makeup kit containing the makeup cosmetic defined in any one of (1) to (5) and a top coating agent containing methylphenylpolysiloxane having a viscosity of 1,000 to 7,000 cs at 25° C.;

(7) The makeup kit according to claim (6), wherein a content of the methylphenylpolysiloxane is 50.0 to 100 mass % relative to a total weight of the top coating agent;

(8) The makeup kit according to claim (6) or (7), wherein the methylphenylpolysiloxane has a refractive index of 1.40 to 1.60 (25° C.); and (9) A makeup method comprising applying the makeup cosmetic using the makeup kit defined in any one of (6) to (8), and then applying the top coating agent over the makeup cosmetic.

Effects of the Invention

The makeup cosmetic of the present invention is capable of forming a coating which is soft and has a moist texture owing to use of polyisobutylene which is a hydrocarbon-based resin as a coating formation component. Further, combined use of the polyisobutylene with a volatile hydrocarbon oil enables to form a coating which is soft, highly adhesive, and excellent in color transfer prevention effect. Further, use of polyisobutylene having a relative mass (molecular weight) within a specific range of 30,000 to 100,000 enables to attain good use feeling without causing stringing and being free from a material odor as of polyisoprene.

Further, a top coating agent of the present invention is capable of maintaining good glossiness for a long time, suppressing color transfer, and having excellent use feeling by not causing smudge, running, and stickiness. Therefore, the top coating agent is suitably used as a makeup kit when used in combination with the makeup cosmetic.

MODES FOR CARRYING OUT THE INVENTION

[1. Makeup Cosmetic]

A makeup cosmetic of the present invention contains as essential components polyisobutylene having a relative mass (Mv) of 30,000 to 100,000 and a volatile hydrocarbon oil. As used herein, the relative mass (molecular weight) means a viscosity average molecular weight of a polymer.

<1-1. Polyisobutylene>

As the polyisobutylene used in the present invention, those having the relative mass (molecular weight) within the above-described range may be used, and commercially available polyisobutylene may also be used.

Examples of the commercially available polyisobutylene include Oppanol B10-SFN (molecular weight: 40,000), Oppanol B11-SFN (molecular weight: 49,000), Oppanol B12-SFN (molecular weight: 55,000), Oppanol B13-SFN (molecular weight: 65,000), and Oppanol B14-SFN (molecular weight: 73,000) each manufactured by BASF, Himol 4H (molecular weight: 40,000), Himol 5H (molecular weight: 50,000), Himol 5.5H (molecular weight: 53,000), Himol 6H (molecular weight: 60,000) each manufactured by Nippon Oil Corporation, and the like.

A content of polyisobutylene in the makeup cosmetic of the present invention is 0.1 to 30 mass %, preferably 1 to 25 mass %, relative to a total weight of the makeup cosmetic. Satisfactory transfer resistance is not attained when the content is less than 0.1 mass %, while stickiness tends to be caused when the content exceeds the upper limit. A more preferred range is varied depending on a product form, and, in the case of producing a lipstick, for example, the content may preferably be 1 to 20 mass %, more preferably 5 to 15 mass %. In the case of producing a foundation, the content may preferably be 1 to 10 mass %, more preferably 2 to 5 mass %.

The makeup cosmetic of the present invention contains as an essential component the polyisobutylene having the relative mass within the predetermined range, but incorporation of polyisobutylene having a relative mass which is outside the predetermined range is not excluded insofar as the polyisobutylene does not impair the effects of the invention. However, in the case of containing polyisobutylene of which a relative mass exceeds 100,000, a content thereof may be less than 50 mass %, preferably less than 30 mass %, more preferably less than 10 mass %, relative to a total weight of the polyisobutylene including the polyisobutylene having the relative mass (Mv) of 30,000 to 100,000. When the polyisobutylene of which the relative mass exceeds 100,000 is contained, the stringing phenomenon undesirably occurs during drying. Most preferably, the makeup cosmetic of the present invention does not substantially contain polyisobutylene of which a relative mass exceeds 100,000.

<1-2. Volatile Hydrocarbon Oil>

Examples of the volatile hydrocarbon oil to be used in the makeup cosmetic of the present invention include volatile oils having 8 to 16 carbon atoms and mixtures thereof. Particularly, the volatile hydrocarbon oils may preferably be selected from branched C8-C16 alkanes, branched C8-C16 esters and mixtures thereof.

Specific examples thereof include isododecane, isodecane, heptane, isohexadecane, and the like, among which isododecane is particularly preferred.

The volatile hydrocarbon oil to be used in the present invention may be those which are commercially available, and specific examples thereof include Marukazole R (isododecane) manufactured by Maruzen Petrochemical, Isopar (isoparaffin) manufactured by Exxon, Permethyl manufactured by PRESSPERS, IP Solvent manufactured by Idemitsu Petrochemical Co., Ltd, and the like.

A content of the volatile hydrocarbon oil in the makeup cosmetic of the present invention may be 3 to 90 mass % relative to a total weight of the makeup cosmetic, preferably 10 to 90 mass %, more preferably 10 to 80 mass %. Spreadability of the cosmetic is deteriorated when the content is less than 3 mass %, and no further improvements in properties are attained when the content exceeds 90 mass %. Particularly, in the case of producing a foundation, the content may further preferably be 15 to 50 mass %, most preferably 20 to 50 mass %.

<1-3. Additive Component in Makeup Cosmetic>

Preferably, the makeup cosmetic of the present invention further contains an organic modified clay mineral and/or a dextrin fatty acid ester. It is possible to increase a viscosity without impairing the use feeling by containing the organic modified clay mineral and/or the dextrin fatty acid ester.

Examples of the organic modified clay mineral include, but are not limited to, those which have heretofore been used for cosmetics, and typical examples thereof include disteardimonium hectorite, stearalkonium hectorite, dimethyldialkyl(14-18)ammonium bentonite, benzyldimethylstearylammonium hectorite, and the like. The organic modified clay mineral to be used in the present invention may be those which are commercially available, and, for example, Benton 38VCG manufactured by Elementis Specialties is preferably used.

A content of the organic modified clay mineral in the makeup cosmetic of the present invention may be 0.1 to 20 mass 4, preferably 0.1 to 10 mass %, more preferably 0.1 to 5 mass %, relative to the total amount of the makeup cosmetic. The intended effect is not attained when the content is less than 0.1 mass %, and undesirable powderiness and a lack of glossiness tend to be caused when the content exceeds 20 mass %.

The dextrin fatty acid ester to be used in the present invention is an ester of dextrin and a higher fatty acid and may partially be selected from those of C12-C22 fatty acid esters. The higher fatty acid ester may preferably contain a C6-C10 fatty acid insofar as the C12-C22 fatty acid is contained. Examples of the dextrin fatty acid ester include dextrin palmitate, dextrin myristate, and dextrin (palmitate/ethylhexanoate), and commercially available products thereof include Rheopearl KL, Rheopearl KL2, Rheopearl TT, Rheopearl TT2, Rheopearl MKL2, Rheopearl ISK2 (all manufactured by Chiba Flour Milling Co., Ltd.), and the like.

A content of the dextrin fatty acid ester may be within a range of 0.1 to 30 mass %, preferably 0.1 to 20 mass %, more preferably 0.1 to 10 mass %, relative to the total amount of the makeup cosmetic. The intended effect is not attained when the content is less than 0.1 mass %, and stickiness tends to be caused when the content exceeds 30 mass %.

Preferably, the makeup cosmetic of the present invention further contains a solid oil component and/or a powder. When the solid oil component and/or the powder are/is contained, stickiness of the cosmetic is suppressed to further improve the use feeling.

The solid oil component to be used in the makeup cosmetic of the present invention may be those which have heretofore been used for cosmetics and the like, and examples thereof include a microcrystalline wax, ceresin, Candelilla wax, and the like.

A content of the solid oil component may be within a range of 0.1 to 50 mass %, preferably 0.1 to 30 mass %, more preferably 0.1 to 20 mass, relative to the total amount of the makeup cosmetic. The intended effect is not attained when the content is less than 0.1 mass %, and glossiness tends to be diminished when the content exceeds 50 mass %.

A powder to be used in the makeup cosmetic of the present invention may be those which have heretofore been used for cosmetics and the like, and examples thereof include mica, sericite, silica, and the like.

A content of the powder may be within a range of 1 to 50 mass %, preferably 1 to 40 mass Q, more preferably 1 to 30 mass, relative to the total amount of the makeup cosmetic. The intended effect is not attained when the content is less than 1 mass %, and powderiness and a lack of glossiness tend to be caused when the content exceeds 50 mass %.

Further, in the present invention, various components to be used in ordinary makeup cosmetics may be contained in addition to the above-described components within a range which does not impair the effects of the present invention.

For example, in the case where the makeup cosmetic of the present invention is used as a lipstick, a color material is ordinarily contained in addition to the above-described components. The color material may be those which are ordinarily used for lipsticks and may be in the form of a powder or a lake (in a state where an oil is kneaded thereinto).

Preferably, the makeup cosmetic of the present invention may not contain a silicone-based resin. When the silicone-based resin is contained, a coating to be formed tends to be hardened, and tautness and stiffness tends to be caused.

The makeup cosmetic of the present invention may be provided in the form of a lipstick, an eye-shadow, a foundation, or the like. In any one of the forms, the makeup cosmetic exhibits excellent transfer resistance and is less subject to makeup deterioration and excellent in use feeling as compared to the conventional oily makeup cosmetics.

[2. Top Coating Agent]

The top coating agent of the present invention contains methylphenylpolysiloxane having a viscosity of 1,000 to 7,000 cs at 25° C.

The top coating agent of the present invention may preferably have a viscosity of about 3,000 to 8,000 cs as a viscosity of the composition as a whole from the viewpoint of usability.

<2-1. Methylphenylpolysiloxane>

The methylphenylpolysiloxane to be contained in the top coating agent of the present invention is a colorless and transparent liquid oil component which may have a viscosity at 25° C. of 1,000 to 7,000 cs, preferably 1,000 to 6,000 cs, more preferably 1,000 to 5,000 cs.

Smudge and running tend to be caused when the viscosity is lower than 1,000 cs, resulting in a product which has a poor glossiness-lasting property. Further, when the viscosity is higher than 7,000 cs, the base makeup cosmetic is scraped off when the top coating agent is applied due to the viscosity of the top coating agent to sometimes cause color transfer.

Particularly, in order to maintain transparent glossiness and to successfully prevent the color transfer to a cup or the like, the methylphenylpolysiloxane to be used may have a refractive index (25° C.) of about 1.40 to 1.60, more preferably 1.45 to 1.55.

The methylphenylpolysiloxane to be used in the present invention is not particularly limited insofar as it is polysiloxane containing a methyl group and a phenyl group and satisfies the above-described viscosity conditions (preferably the refractive index conditions, too), and, more specifically, the methylphenylpolysiloxane contains a mixture of one or more kinds of compounds represented by the following general formula (I).

bination of two or more thereof. Examples of the commercially available product include KF50-54 HV (viscosity: about 5,000 cs) manufactured by Shin-Etsu Chemical, Co., Ltd. and the like. In the case of using two or more kinds in combination, the viscosity of the mixture may be within the above-described predetermined range.

A content of the methylphenylpolysiloxane in the top coating agent of the present invention may be 50 to 100 mass %, preferably 60 to 100 mass %, more preferably 80 to 100 mass %, further preferably about 95 mass %, relative to a total amount of the top coating agent. The content of less than 50 mass % is not preferred from the viewpoints of glossiness and color transfer prevention.

The methylphenylpolysiloxane to be used in the top coating agent of the present invention has a property of hardly diffusible on the skin as compared to dimethylpolysiloxane or the like which has generally been used for conventional top coating agents. Therefore, the top coating agent is naturally spread on the lipstick without causing smudge when it is applied over the lipstick and, therefore, is suitably used as a lip coat. Further, though it is necessary to contain a predetermined amount of a powder component such as silica in order to prevent running in the conventional top coating agents using low viscosity silicone oil, the methylphenylpolysiloxane to be used in the present invention has the high viscosity of 1,000 cs or more and, therefore, is capable of preventing the running or the like without containing other components.

In the meantime, Patent Document 9 mentioned above includes the description which denies the use of methylphenylpolysiloxane having high viscosity as in the present invention (paragraph 0009). However, the top coating agent of the present invention is particularly suitable for the combined use with the above-described specific makeup cosmetic, i.e. the makeup cosmetic containing polyisobutylene and volatile hydrocarbon oil, due to the high-viscosity methylphenylpolysiloxane contrary to the findings of Patent Document 9. Those skilled in the art cannot anticipate that the incorporation of the methylphenylpolysiloxane having high viscosity into a top coating agent as in the present invention enables the top coating agent to exhibit the excel-

[Chemical formula 1]

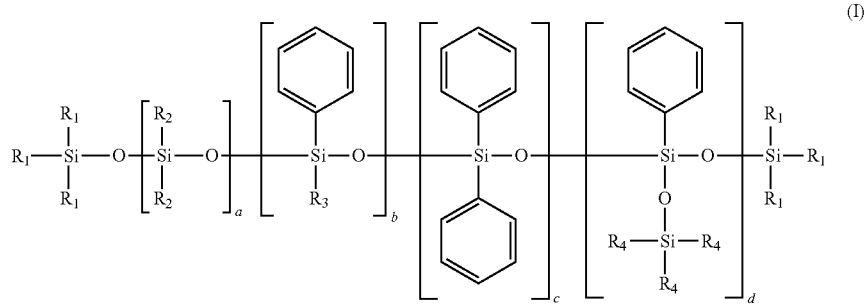

(I)

In the above formula, each of $R_1$ to $R_4$ is a methyl group; "a" is an integer within a range of 1 to 900; and "b+c+d" is an integer within a range of 1 to 900.

As the methylphenylpolysiloxane represented by the above formula (I), those having various molecular weights and viscosities are commercially available, and the commercially available product may be used alone or in comlent color transfer prevention effect especially in the case of applying the top coating agent on a cosmetic having high coating property.

<2-2. Additive Component in Top Coating Agent>

The top coating agent of the present invention may contain an oil component other than methylphenylpolysiloxane or a powder component. Examples of the oil component include a hydrocarbon oil and a silicone oil which are ordinarily used for cosmetics and the like, and a content thereof is within a range which does not impair the effects of the present invention. Preferably, the top coating agent of the present invention may not contain dimethylpolysiloxane having low viscosity from the viewpoints of preventing smudge and running and maintaining glossiness.

Examples of the powder component include an inorganic powder such as anhydrous silicate and a pearlescent agent, an organic resin powder, and the like. In addition, a component which is used in ordinary oily cosmetics, such as a hydrocarbon, a higher fatty acid ester, an animal or plant oil, an antioxidant, a fragrance material, a pigment, a UV absorber, a moisturizing agent, and the like may appropriately be contained in an amount which does not impair the effects of the present invention.

[3. Makeup Kit and Makeup Method Using the Same]

With the combined use of the makeup cosmetic of the present invention and the top coating agent of the present invention described above, it is possible to further improve glossiness, color transfer resistance, and usability as compared to the case of using the makeup cosmetic alone, and, also, it is possible to considerably improve glossiness-lasting property over time.

Therefore, the present invention also provides a makeup kit including the makeup cosmetic and the top coating agent. The makeup kit of the present invention may be provided in any form and, for example, may be provided in the form in which the makeup cosmetic of the present invention is housed in one of sections of a container having at least two sections and the top coating agent is housed in another one of the sections.

Further, the present invention provides a makeup method using the makeup kit. The makeup method according to the present invention includes applying the makeup cosmetic and then applying the top coating agent. A palette, chip, a brush member, or a finger may be used for applying each of the makeup cosmetic and the top coating agent without particular limitation thereto, and a spatular palette is suitably used from the viewpoint of applying the top coating agent of the present invention having high viscosity without removing a lipstick or the like which is a base.

With the use of the makeup kit of the present invention, particularly favorable glossiness lasts for a long time, and it is possible to considerably suppress color transfer to a cup or the like.

EXAMPLES

The present invention will be described in more details in conjunction with Examples, and the present invention is not limited at all by the Examples. Contents are indicated by mass % unless otherwise specified.

Hereinafter, Examples and Comparative Examples relating to makeup cosmetics will be described first (Examples 1 to 3 and Comparative Examples 1 to 11), and then Examples and Comparative Examples relating to top coating agents to be used in combination with the makeup cosmetics as a makeup kit (Examples 4 to 5 and Comparative Examples 12 to 14) will be described.

Makeup Cosmetics: Example 1 and Comparative Examples 1 to 5

Liquid lipsticks were prepared based on formulations shown in Table 1 below, and properties thereof were evaluated in accordance with an evaluation method and evaluation criteria. The results are also shown in Table 1.

(Evaluation Method)

The samples were used by panelist (10 person), and stickiness, tautness, glossiness, finish evenness, smell, transfer resistance, temporal change, and removal easiness by cleansing were evaluated by 5-grade sensory evaluation (score). The judgment was made by a score average value based on the evaluation criteria described below. The transfer resistance was evaluated by directly pressing the lips to a ceramic coffee cup.

(Score)
5: Remarkably excellent
4: Excellent
3: Standard
2: Poor
1: Very poor (Evaluation Criteria)
⊙: Evaluation value (average value) of 4.0 or more and 5.0 or less
○: Evaluation value (average value) of 3.0 or more and less than 4.0
Δ: Evaluation value (average value) of 2.0 or more and less than 3.0
x: Evaluation value (average value) of 1.0 or more and less than 2.0

TABLE 1

|  | Example 1 | Comparative Example 1 | Comparative Example 2 | Comparative Example 3 | Comparative Example 4 | Comparative Example 5 |
| --- | --- | --- | --- | --- | --- | --- |
| Polyisobutylene (Mv 55000) | 16.5 | — | — | — | — | — |
| Alkyldimethicone acrylate[1)] | — | 16.5 | — | — | — | — |
| Acryl silicone dendrimer[2)] | — | — | 16.5 | — | — | — |
| Highly polymerized methylpolysiloxane[3)] | — | — | — | 16.5 | — | — |
| Trimethylsiloxy silicate[4)] | — | — | — | — | 16.5 | — |
| Polyisoprene[5)] | — | — | — | — | — | 16.5 |
| Isododecane | 58 | 19.5 | 58 | — | 58 | 58 |
| Volatile isoparaffin | — | — | — | 58 | — | — |
| Decamethyl cyclopentasiloxane | — | 38.5 | — | — | — | — |
| Microcrystalline wax | 4 | 4 | 4 | 4 | 4 | 4 |
| Mineral oil | 10 | 10 | 10 | 10 | 10 | 10 |
| Triisostearic acid PEG-20 Hydrogenated castor oil | 1 | 1 | 1 | 1 | 1 | 1 |
| Butylene glycol | 1.5 | 1.5 | 1.5 | 1.5 | 1.5 | 1.5 |
| Distear-dimonium hectorite | 5 | 5 | 5 | 5 | 5 | 5 |
| Mica | 2 | 2 | 2 | 2 | 2 | 2 |

TABLE 1-continued

|  | Example 1 | Comparative Example 1 | Comparative Example 2 | Comparative Example 3 | Comparative Example 4 | Comparative Example 5 |
|---|---|---|---|---|---|---|
| Red iron oxide | 0.5 | 0.5 | 0.5 | 0.5 | 0.5 | 0.5 |
| Titanium oxide | 1 | 1 | 1 | 1 | 1 | 1 |
| Red 202 | 0.5 | 0.5 | 0.5 | 0.5 | 0.5 | 0.5 |
| Total (%) | 100 | 100 | 100 | 100 | 100 | 100 |
| Stickiness | ○ | ○ | ○ | Δ | ○ | ○ |
| Tautness | ⊙ | X | X | Δ | X | Δ |
| Glossiness | ○ | X | X | X | X | Δ |
| Finish evenness | ⊙ | X | Δ | X | X | Δ |
| Smell | ○ | ○ | ○ | ○ | ○ | X |
| Color transfer prevention effect | ○ | ○ | ○ | X | ○ | ○ |
| Flakiness over time | ⊙ | X | Δ | Δ | X | ○ |
| Removal easiness by oil cleansing | ○ | Δ | X | Δ | Δ | Δ |

1) Alkyldimethicone acrylate: Silicone KP545 manufactured by Shin-Etsu.
2) Acryl silicone dendrimer: FA40021D manufactured by Toray-Dow.
3) Highly polymerized methylpolysiloxane: Silicone G-20-IP manufactured by Shin-Etsu.
4) Trimethylsiloxysilicate: X-21-5595 manufactured by Shin-Etsu,
5) Polyisoprene: Resin 70P manufactured by Nikko Rika Corporation.

As is apparent from Table 1, tautness, finish unevenness, and poor glossiness were observed with Comparative Examples 1 to 4 containing the silicone-based resin particularly. Further, as to the texture, Comparative Examples 1 to 4 flaked off over time, and there was a tendency that removal thereof by oil cleansing was difficult. Further, Comparative Example 5 containing polyisoprene had a particularly unpleasant smell and was unsatisfactory in terms of tautness, glossiness, finish evenness, and removal easiness by oil cleansing. In contrast, Example 1 containing the polyisobutylene having relative mass of 55,000 together with the volatile hydrocarbon oil (isododecane) attained good results in all of the evaluation items.

Makeup Cosmetic: Example 2 and Comparative Examples 6 to 10

Liquid lipsticks were prepared based on the formulations shown in Table 2 below, and properties thereof were evaluated in accordance with the above-described evaluation method and evaluation criteria. The results are also shown in Table 2.

TABLE 2

|  | Example 2 | Comparative Example 6 | Comparative Example 7 | Comparative Example 8 | Comparative Example 9 | Comparative Example 10 |
|---|---|---|---|---|---|---|
| Polyisobutene (Mv 1000) | — | 10 | — | 5 | — | — |
| Polyisobutylene (Mv 55000) | 10 | — | — | — | 5 | 10 |
| Polyisobutylene (Mv 200000) | — | — | 10 | 5 | 5 | — |
| Isododecane | 60 | 60 | 60 | 60 | 60 | — |
| Dextrin palmitate | 3 | 3 | 3 | 3 | 3 | 3 |
| Microcrystalline wax | 3 | 3 | 3 | 3 | 3 | 3 |
| Mineral oil | — | — | — | — | — | 60 |
| Diisostearyl malate | 2 | 2 | 2 | 2 | 2 | 2 |
| Distear-dimonium hectorite | 2 | 2 | 2 | 2 | 2 | 2 |
| Propylene carbonate | 0.6 | 0.6 | 0.6 | 0.6 | 0.6 | 0.6 |
| Mica | 15 | 15 | 15 | 15 | 15 | 15 |
| Titanium-coated mica | 2.4 | 2.4 | 2.4 | 2.4 | 2.4 | 2.4 |
| Red iron oxide | 0.5 | 0.5 | 0.5 | 0.5 | 0.5 | 0.5 |
| Titanium oxide | 0.5 | 0.5 | 0.5 | 0.5 | 0.5 | 0.5 |
| Red 202 | 1 | 1 | 1 | 1 | 1 | 1 |
| Total (%) | 100 | 100 | 100 | 100 | 100 | 100 |
| Stickiness | ○ | X | ○ | Δ | ○ | X |
| Stringing during drying | ○ | ○ | X | X | X | Δ |
| Color lasting property | ⊙ | X | Δ | Δ | Δ | X |
| Color transfer prevention effect | ⊙ | X | ○ | Δ | ○ | X |
| Removal easiness by oil cleansing | ○ | ⊙ | X | X | X | ○ |

From the results shown in Table 2, it is apparent that Comparative Example 6 containing the polyisobutylene having relative mass of 1,000 alone caused stickiness, and transfer resistance and color-lasting property thereof were unsatisfactory. Further, Comparative Examples 7 to 9 containing the polyisobutylene having relative mass exceeding 100,000 caused the stringing phenomenon during drying, and removal by oil cleansing was difficult. Further, Comparative Example 10 containing the polyisobutylene having relative mass of 55,000 and not containing the volatile hydrocarbon oil caused stickiness and had considerably poor transfer resistance and color maintaining property.

Makeup Cosmetic: Example 3 and Comparative Example 11

Liquid foundations were prepared based on formulations shown in Table 3 below, and a color change before and after a rubbing treatment using a white cloth of each of the samples was measured in accordance with the following method.

(Measurement Method)
(1) A predetermined amount of the sample was applied on an artificial leather and dried.
(2) A JIS standard white cloth was attached to an application robot, and the artificial leather on which the sample was applied was rubbed with the white cloth at a constant force.
(3) A color difference was measured by using a spectroscopic colorimeter (CM-2600d/manufactured by Konica Minolta).

TABLE 3

| Classification | Material generic name | Comparative Example 11 | Example 3 |
|---|---|---|---|
| Alcohol | Alcohol | 18 | 18 |
| Dispersion agent | Isostearic acid | 0.5 | 0.5 |
| Oil component | Cyclomethicone | 43.87 | — |
|  | Isododecane | — | 43.91 |
| Coating agent | 3-[tris(trimethylsiloxy)-silyl] pullulan propylcarbamate | 4.5 | — |
|  | Polyisobutylene (MV 55000) | — | 4.5 |
| UV absorber | Octyl methoxycinnamate | 5 | 5 |
|  | Octocrylene | 0.4 | 0.4 |
| Powder | Alkyl-modified silicone resin-coated iron oxide | 1.49 | 1.49 |
|  | N-octylsilylated titanium oxide | 9 | 9 |
|  | Alkyl-modified silicone resin-coated iron oxide•titanium oxide sintered material | 8 | 8 |
|  | Methicone (vinyldimethicone) crosspolymer | 1 | 1 |
|  | Anhydrous silicate | 1 | 1 |
|  | Dimethylsilylated anhydrous silicate | 0.2 | 0.2 |
|  | Titanium oxide | 7 | 7 |
| Fragrance | Fragrance | 0.04 | — |
|  | Total | 100 | 100 |
|  | Color difference ΔE*ab | 4.4 | 3.3 |
|  | Secondary adhesion prevention effect | Δ | ⊙ |

A color change caused by the rubbing with white cloth was great in Comparative Example 11 containing the silicone-based resin and the silicone oil to show the unsatisfactory transfer resistance, but Example 3 containing the combination of polyisobutylene and isododecane was suppressed in color change to show excellent transfer resistance.

Top Coating Agent: Examples 4 and 5 and Comparative Examples 12 to 14

A makeup cosmetic (lipstick) having a composition identical to Example 2 was prepared.

TABLE 4

|  | Lipstick |
|---|---|
| Hydrocarbon-based resin (polyisobutylene: Mv 55000) | 10 |
| Isododecane | 60 |
| Dextrin palmitate | 3 |
| Microcrystalline wax | 3 |
| Diisostearyl malate | 2 |
| Distear-dimonium hectorite | 2 |
| Propylene carbonate | 0.6 |
| Mica | 15 |
| Pearlescent agent | 2.4 |
| Color material | 2 |
| Total (%) | 100 |

The lipstick was applied on panelists (10 persons), and then each of the samples of the top coating agents having compositions shown in Table 5 below was applied, followed by evaluation in accordance with a method and criteria described below.

(Evaluation Method)

Glossiness immediately after application, color transfer resistance, smudge, running, stickiness, and glossiness-lasting property were evaluated by 5-grade sensory evaluation (score). The judgment was made by a score average value based on the evaluation criteria described below. The color transfer resistance was evaluated by directly pressing the lips to a ceramic coffee cup.

(Score)
5: Remarkably excellent
4: Excellent
3: Standard
2: Poor
1: Very poor (Evaluation Criteria)
⊙: Evaluation value (average value) of 4.0 or more and 5.0 or less
○: Evaluation value (average value) of 3.0 or more and less than 4.0
Δ: Evaluation value (average value) of 2.0 or more and less than 3.0
x: Evaluation value (average value) of 1.0 or more and less than 2.0

TABLE 5

|  | Example 4 | Example 5 | Comparative Example 12 | Comparative Example 13 | Comparative Example 14 |
|---|---|---|---|---|---|
| Dimethyldiphenyl polysiloxane 5000 cs | 95.99 | — | — | — | — |
| Dimethyldiphenyl polysiloxane 1000 cs | — | 95.99 | — | — | — |
| Dimethyl polysiloxane 5000 cs | — | — | 95.99 | — | — |
| Dimethyldiphenyl polysiloxane 300 cs | — | — | — | 95.99 | — |

TABLE 5-continued

| | Example 4 | Example 5 | Comparative Example 12 | Comparative Example 13 | Comparative Example 14 |
|---|---|---|---|---|---|
| Polyisobutylene (Mv 1000) | — | — | — | — | 50 |
| Diisostearyl malate | — | — | — | — | 45.99 |
| Anhydrous silicate | 3 | 3 | 3 | 3 | 3 |
| Pearlescent agent | 1 | 1 | 1 | 1 | 1 |
| Color material | 0.01 | 0.01 | 0.01 | 0.01 | 0.01 |
| Total | 100 | 100 | 100 | 100 | 100 |
| Immediate glossiness | ⊙ | ○ | ⊙ | Δ | ○ |
| Color transfer to cup | ⊙ | ⊙ | ⊙ | ○ | X |
| Smudge | ⊙ | ○ | Δ | ○ | ○ |
| Running | ⊙ | ○ | Δ | X | ○ |
| Stickiness | ○ | ⊙ | Δ | ⊙ | X |
| Glossiness-lasting property | ⊙ | ○ | Δ | X | Δ |

As is apparent from the results shown in Table 5, each of Examples 4 and 5 containing the methylphenylpolysiloxane having the viscosity higher than 1,000 cs was free from color transfer to the cup, attained favorable glossiness and glossiness-lasting property, and was excellent in use feeling including running or stickiness. In contrast, Comparative Example 12 containing the high-viscosity dimethylpolysiloxane was particularly inferior in use feeling and glossiness-lasting property, and Comparative Example 13 containing the low-viscosity methylphenylpolysiloxane caused running and had the poor glossiness-lasting property. Comparative Example 14 containing the hydrocarbon-based oil component caused color transfer and stickiness.

In view of the above, it is confirmed that the top coating agents of Examples 4 and 5 are suitably used for the makeup cosmetics containing the hydrocarbon-based resin (polyisobutylene).

Hereinafter, formulation examples of the makeup cosmetics (Formulation Examples 1 to 5) and a formulation example of the top coating agent (Formulation Example 6) of the present invention are exemplified. The present invention is not limited by the formulation examples at all and is of course specified by the appended claims.

Formulation Example 1: Liquid Lipstick

| Components | Content (mass %) |
|---|---|
| (1) Isododecane | 60 |
| (2) Polyisobutylene (Mv 1000) | 3 |
| (3) Polyisobutylene (Mv 55000) | 7 |
| (4) Dextrin palmitate | 3 |
| (5) Microcrystalline wax | 3 |
| (6) Diisostearyl malate | 2 |
| (7) Distear-dimonium hectorite | 2 |
| (8) Propylene carbonate | q.s. |
| (9) Dipropylene glycol | q.s. |
| (10) Titanium oxide | 2 |
| (11) Red 202 | 1.5 |
| (12) Yellow iron oxide | 0.3 |
| (13) Black iron oxide | 0.1 |
| (14) Mica | 15 |

Production method: The liquid lipstick was obtained by melting (1) to (6) by mixing and heating, adding a part of (1) and a mixed dispersion of (7) and (8), and subjecting (9) to (14) to uniform mixed dispersion.

Formulation Example 2: Liquid Lipstick

| Components | Content (mass %) |
|---|---|
| (1) Isododecane | 55 |
| (2) Polyisobutylene (Mv 65000) | 5 |
| (3) Dextrin palmitate | 10 |
| (4) Microcrystalline wax | 20 |
| (5) Diisostearyl malate | 3 |
| (6) Titanium oxide | 1 |
| (7) Red 202 | 1.5 |
| (8) Yellow iron oxide | 0.3 |
| (9) Black iron oxide | 0.2 |
| (10) Mica | 4 |

Production method: The liquid lipstick was obtained by melting (1) to (5) by mixing and heating, and subjecting (6) to (10) uniform mixed dispersion.

Formulation Example 3: Concealer

| Components | Content (mass %) |
|---|---|
| (1) Ceresin | 15 |
| (2) Microcrystalline wax | 1 |
| (3) Polyisobutylene (Mv 55000) | 15 |
| (4) Isohexadecane | 18 |
| (5) Isododecane | 10 |
| (6) Mineral oil | 10 |
| (7) Titanium oxide | 10 |
| (8) Red iron oxide | 1 |
| (9) Polymethyllsilsesquioxane | 10 |
| (10) Polymethylmethacrylate | 10 |

Production method: The concealer was obtained by melting (1) to (6) by mixing and heating, adding (7) to (10), followed by uniform mixed dispersion.

Formulation Example 4: Mascara

| Components | Content (mass %) |
|---|---|
| (1) Microcrystalline wax | 5 |
| (2) Mineral oil | 5 |
| (3) Light isoparaffin | 40 |
| (4) Polyisobutylene (Mv 55000) | 20 |
| (5) Distear-dimonium hectorite | 10 |
| (6) Isostearic acid | 3 |
| (7) Iron oxide | 6 |

| Components | Content (mass %) |
|---|---|
| (8) Ethyl alcohol | q.s. |
| (9) Butylene glycol | q.s. |

Production method: The mascara was obtained by melting (1) to (5) by mixing and heating, adding (6) and (7), followed by uniform mixed dispersion, adding (8) and (9), followed by uniform mixed dispersion.

Formulation Example 5: Oily Eye Shadow

| Components | Content (mass %) |
|---|---|
| (1) Microcrystalline wax | 10 |
| (2) Sucrose fatty acid ester | 5 |
| (3) Ceresin | 5 |
| (4) Triethylhexanoin | 2 |
| (5) Polyisobutylene (Mv 1000) | 5 |
| (6) Polyglyceryl diisostearate | 2 |
| (7) Isododecane | 30 |
| (8) Polyisobutylene (Mv 55000) | 5 |
| (9) Talc | 10 |
| (10) Synthetic mica | 5 |
| (11) Nylon powder | 5 |
| (12) Colcothar-coated mica titanium | 10 |
| (13) Mica titanium | 5 |
| (14) Black iron oxide | 1 |

Production method: The oily eye shadow was obtained by melting (1) to (8) by mixing and heating, adding (9) to (14), followed by uniform mixed dispersion.

Formulation Example 6: Oily Lip Coat

| Components | Content (mass %) |
|---|---|
| (1) Methylphenylpolysiloxane 3,000 cs | 95.99 |
| (2) Anhydrous silicate | 3 |
| (3) Hydrophobized pearlescent agent | 1 |
| (4) Color material | 0.01 |

Production method: The lip coat was prepared by wetting the anhydrous silicate with the methylphenylpolysiloxane at a room temperature, adding the pearlescent agent and the color material, followed by dispersion with stirring.

The invention claimed is:

1. A makeup kit, said kit comprising an oily makeup cosmetic composition, and a top coating agent for applying over said oily makeup cosmetic composition, wherein said oily makeup cosmetic composition comprises polyisobutylene of 30,000 to 100,000 relative mass, a second polyisobutylene having relative mass exceeding 100,000 in an amount of less than 10% by mass relative to total amount of polyisobutylenes, and a volatile hydrocarbon oil; and said top coating agent consists essentially of 50 to 100% by mass relative to a total amount of said top coating agent of a methyiphenylpolysiloxane having a viscosity of 1,000 to 5,000 cs at 25° C.

2. The makeup kit according to claim 1, wherein the methylphenylpolysiloxane has a refractive index of 1.40 to 1.60 at 25° C.

3. The makeup kit according to claim 1, wherein said volatile hydrocarbon oil is isododecane.

4. The makeup kit according to claim 1, wherein said oily makeup cosmetic composition further comprises an organic modified clay mineral and/or a dextrin fatty acid ester.

5. The makeup kit according to claim 1, wherein said oily makeup cosmetic composition further comprises a solid oil component and/or a powder.

6. The makeup kit according to claim 1, wherein said oily makeup cosmetic composition is a lipstick, an eye shadow, or a makeup foundation.

* * * * *